(12) United States Patent
Iida et al.

(10) Patent No.: US 8,445,079 B2
(45) Date of Patent: May 21, 2013

(54) OPTICAL FILM, IMAGE DISPLAY DEVICE, DIETHYNYLFLUORENE, AND POLYMER THEREOF

(75) Inventors: Toshiyuki Iida, Ibaraki (JP); Yutaka Ohmori, Ibaraki (JP); Miyuki Kurogi, Ibaraki (JP)

(73) Assignee: Nitto Denko Corporation, Ibaraki-shi, Osaka (JP)

( * ) Notice: Subject to any disclaimer, the term of this patent is extended or adjusted under 35 U.S.C. 154(b) by 344 days.

(21) Appl. No.: 12/601,198

(22) PCT Filed: Apr. 9, 2008

(86) PCT No.: PCT/JP2008/056973
§ 371 (c)(1),
(2), (4) Date: Nov. 20, 2009

(87) PCT Pub. No.: WO2008/142921
PCT Pub. Date: Nov. 27, 2008

(65) Prior Publication Data
US 2010/0182693 A1    Jul. 22, 2010

(30) Foreign Application Priority Data

May 24, 2007 (JP) ................................ 2007-137782
Nov. 27, 2007 (JP) ................................ 2007-305480

(51) Int. Cl.
*C09K 19/00* (2006.01)
(52) U.S. Cl.
USPC ............ 428/1.1; 428/1.2; 428/1.31; 428/917; 349/1; 349/117; 349/193; 528/271; 528/403; 528/405; 528/406; 359/483.01; 359/489.01; 252/301.16; 252/301.22; 427/99.4
(58) Field of Classification Search
CPC ................................ C09K 19/42; C09K 19/38
USPC .......... 528/271, 272, 403, 405, 406; 428/1.1, 428/1.2, 1.31, 1.55, 220, 221, 917; 427/99.4, 427/103, 372.2, 385.5; 359/483.01, 489.01; 349/1, 69, 70, 96, 117, 118, 120, 167, 176, 349/193, 194, 200, 201; 252/301.16, 301.32
See application file for complete search history.

(56) References Cited

U.S. PATENT DOCUMENTS
5,763,636 A    6/1998 Kreuder et al.
2007/0164273 A1    7/2007 Gerhard et al.

FOREIGN PATENT DOCUMENTS

| JP | 2000-508686 A | 7/2000 |
|---|---|---|
| JP | 2000-511296 A | 8/2000 |
| JP | 2002-221622 A | 8/2002 |
| JP | 2003-096072 A | 4/2003 |
| JP | 2005 015442 A | * 1/2005 |
| JP | 2006-003715 A | 1/2006 |
| JP | 2007-526634 A | 9/2007 |
| WO | 2005/084081 A1 | 9/2005 |

OTHER PUBLICATIONS

Machine translation of JP 2005 015442.*
Machine translation of JP 2003 096072.*
Machine translation of JP 2006 003715.*
International Search Report of PCT/JP2008/056973, mailing date of Jun. 17, 2008.
Korean Office Action dated Nov. 16, 2011, issued in corresponding Korean Patent Application No. 10-2009-7020318. w/partial English tanslation.
Chinese Office Action dated Jan. 26, 2011, issued in corresponding Chinese Patent Application No. 200880017322X.

* cited by examiner

*Primary Examiner* — Frances Tischler
(74) *Attorney, Agent, or Firm* — Westerman, Hattori, Daniels & Adrian, LLP

(57) ABSTRACT

An object of the present invention is to provide an optical film exhibiting a preferable wavelength dispersion and capable of being formed comparatively thinly.
The present invention is an optical film containing the repeating unit represented by the following general formula (II).
In the formula (II), A, A', B, and B' each denote a substituent, a, a', b, and b' denote the number of substituents of the corresponding A, A', B, and B'. A, A', B and B' each independently denote a halogen or an alkyl group having 1 to 4 carbon atoms. $R^1$ and $R^2$ denote a halogen, an alkyl group having 1 to 10 carbon atoms, and the like. X denotes —CO—, —SO$_2$—, and the like.

(II)

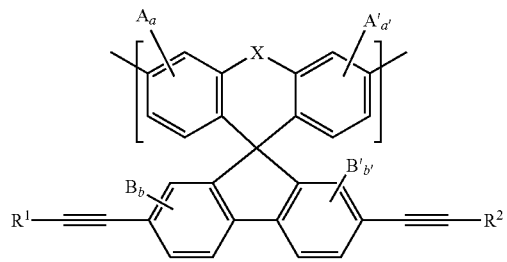

14 Claims, No Drawings

OPTICAL FILM, IMAGE DISPLAY DEVICE, DIETHYNYLFLUORENE, AND POLYMER THEREOF

TECHNICAL FIELD

The present invention relates to an optical film, an image display device, and diethynylfluorene used for a forming material of the optical film and a polymer thereof.

BACKGROUND ART

A retardation film is an optical film for realizing a wider viewing angle or the like of a liquid crystal display. The retardation value of the retardation film depends on wavelength. The wavelength dispersion of the retardation value is roughly classified into the following three kinds. The first is a retardation film which exhibits wavelength dispersion such that a retardation value is larger on the shorter wavelength side (hereinafter referred to as "normal dispersion"), the second is a retardation film which exhibits wavelength dispersion such that a retardation value scarcely changes ranging from the short wavelength side to the long wavelength side (hereinafter referred to as "flat dispersion"), and the third is a retardation film which exhibits wavelength dispersion such that a retardation value is smaller on the shorter wavelength side (hereinafter referred to as "reverse dispersion").

Here, the normal dispersion and the reverse dispersion exhibit optical properties such that the wavelength dependence of the retardation value is large, and the flat dispersion exhibits optical property such that the wavelength dependence of the retardation value is small.

As the retardation film exhibiting the flat dispersion, a norbornene-based film (for example, trade name "ARTON FILM", manufactured by JSR Corporation) obtained by film-forming and drawing a norbornene-based resin has been conventionally known. However, the norbornene-based film is so comparatively thick as approximately 60 to 80 μm that, accordingly, a liquid crystal display having this optical film becomes comparatively thick and heavy.

On the other hand, it is known that a retardation film containing polyimide may be formed by coating a solution, which contains the polyimide, on a base material, and the retardation film containing polyimide exhibits predetermined retardation value (Patent Document 1). In the case where the retardation film is formed by coating, the obtained retardation film can be formed comparatively thinly. However, the retardation film containing the polyimide ordinarily exhibits the normal dispersion (that is to say, the retardation film does not exhibit the flat dispersion).

The retardation value in the thickness direction of the retardation film is determined by the expression "Δnxz×thickness". Even if a retardation film having a large Δnxz is comparatively thin, the retardation film exhibits predetermined retardation value. Therefore, a film having a large Δnxz is demanded.

[Patent Document 1] Japanese translation of PCT international application No. 2000-511296

DISCLOSURE OF THE INVENTION

An object of the present invention is to provide an optical film exhibiting a preferable wavelength dispersion of a retardation value and capable of being formed comparatively thinly, and an image display device using the same.

Another object of the present invention is to provide diethynylfluorene appropriate as a material for forming the above-mentioned optical film.

VA (Vertical Alignment) mode has widely prevailed as a liquid crystal cell of a liquid crystal display. The inventors of the present invention examined wavelength dispersion of a retardation value of a liquid crystal cell in this VA mode in detail. As a result, they have found that a liquid crystal cell in VA mode exhibiting the flat dispersion has been increasing in recent years. Thus, a retardation film for compensating this liquid crystal cell is preferably a retardation film exhibiting the flat dispersion. Further, in view of weight saving of the liquid crystal display, a comparatively thin retardation film is preferable. However, as described above, the conventional retardation film has both merits and demerits. For this reason, the inventors of the present invention have earnestly studied about various materials, and found out that the use of a specific polymer allows the above-mentioned object to be achieved.

The present invention provides an optical film containing a polymer having the repeating unit represented by the following general formula (I).

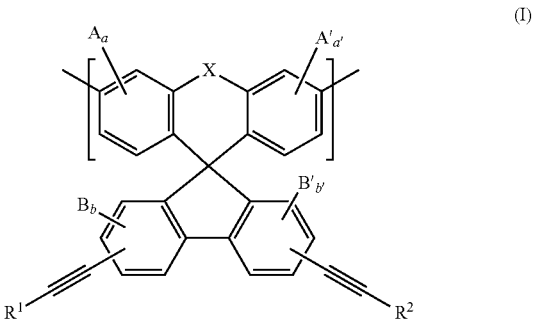

In the formula (I), A, A', B, and B' each denote a substituent, a and a' denote the number of substituents of the corresponding A and A' (an integer of 0 to 3), and b and b' denote the number of substituents of the corresponding B and B' (an integer of 0 to 3). A, A', B and B' each independently denote a halogen or an alkyl group having 1 to 4 carbon atoms. $R^1$ and $R^2$ each independently denote an atom or a group selected from the group consisting of hydrogen, a halogen, an alkyl group having 1 to 10 carbon atoms, a substituted or unsubstituted aryl group, a substituted or unsubstituted vinyl group, a substituted or unsubstituted ethynyl group, an $SiR^3R^4R^5$ group ($R^3$ to $R^5$ each independently denote an alkyl group having 1 to 6 carbon atoms or an aryl group), and a $CR^6R^7$(OH) group ($R^6$ and $R^7$ each independently denote an alkyl group having 1 to 4 carbon atoms). X denotes —$CR^8_2$— ($R^8$ denotes hydrogen, an alkyl group having 1 to 4 carbon atoms, a perfluoro group, or a substituted or unsubstituted aryl group), —$SiR^9_2$— ($R^9$ denotes hydrogen, an alkyl group having 1 to 4 carbon atoms, or a substituted or unsubstituted aryl group), —O—, —$NR^{10}$— ($R^{10}$ denotes hydrogen, an alkyl group having 1 to 4 carbon atoms, or a substituted or unsubstituted aryl group), —CO—, or —$SO_2$—.

With regard to the repeating unit represented by the formula (I), two benzene rings of the main chain portion are bonded by a divalent linking group X. Thus, a polymer into which this repeating unit is introduced is high in rigidity of the main chain. An optical film obtained by forming such a polymer into a film is comparatively large in Δnxz. Accordingly, such an optical film has a desired retardation value even though it is comparatively thin.

In addition, with regard to a polymer having the repeating unit represented by the above-mentioned formula (I), the conjugated system of a fluorene skeleton is extended by a triple bond group (ethynyl group), and the fluorene skeleton is aligned in an approximately orthogonal direction to an extending direction of the main chain. Thus, with regard to an optical film containing the polymer, wavelength dispersion of retardation value thereof approaches the flat dispersion.

The preferable optical film of the present invention has a refractive index Δnxz of 0.005 to 0.070 with a wavelength of 550 nm.

Here, Δnxz=nx−nz. The nx denotes a refractive index in a direction for a maximum refractive index in a plane of the film (x-axis direction), and nz denotes a refractive index in the thickness direction of the film.

The other preferable optical film of the present invention exhibits Rth(450)/Rth(550)<1.06.

The other preferable optical film of the present invention exhibits Rth(650)/Rth(550)≧0.95.

The Rth(450), Rth(550), and Rth(650) denote a retardation value in the thickness direction with a wavelength of 450 nm, 550 nm, and 650 nm, respectively.

As the other preferable optical film of the present invention, the above polymer is a polyester-based polymer.

The present invention provides an image display device comprising the above-mentioned optical film.

Further, the present invention provides a diethynylfluorene represented by the following general formula (X).

[chemical formula 14]

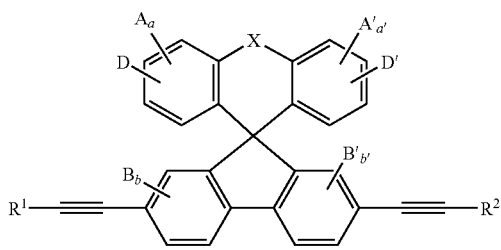

(X)

In the formula (X), A, A', B, and B' each denote a substituent, a and a' denote the number of substituents of the corresponding A and A' (an integer of 0 to 3), and b and b' denote the number of substituents of the corresponding B and B' (an integer of 0 to 3). A, A', B, and B' each independently denote a halogen or an alkyl group having 1 to 4 carbon atoms. D and D' each independently denote an OH group, an NHR group (R denotes hydrogen or an alkyl group having 1 to 4 carbon atoms), a COOH group or an NCO group. $R^1$ and $R^2$ each independently denote an atom or a group selected from the group consisting of hydrogen, a halogen, an alkyl group having 1 to 10 carbon atoms, a substituted or unsubstituted aryl group, a substituted or unsubstituted vinyl group, a substituted or unsubstituted ethynyl group, an $SiR^3R^4R^5$ group ($R^3$ to $R^5$ each independently denote an alkyl group having 1 to 6 carbon atoms or an aryl group), and a $CR^6R^7(OH)$ group ($R^6$ and $R^7$ each independently denote an alkyl group having 1 to 4 carbon atoms). X denotes —$CR^8_2$— ($R^8$ denotes hydrogen, an alkyl group having 1 to 4 carbon atoms, a perfluoro group, or a substituted or unsubstituted aryl group), —$SiR^9_2$— ($R^9$ denotes hydrogen, an alkyl group having 1 to 4 carbon atoms, or a substituted or unsubstituted aryl group), —O—, —$NR^{10}$— ($R^{10}$ denotes hydrogen, an alkyl group having 1 to 4 carbon atoms, or a substituted or unsubstituted aryl group), —CO—, or —$SO_2$—.

The present invention provides a polymer having the above-mentioned diethynylfluorene as a repeating unit.

The optical film of the present invention exhibits the flat dispersion. Therefore, the optical film of the present invention may be appropriately used as a retardation film for compensating a liquid crystal cell in VA mode. Further, the optical film of the present invention has comparatively large Δnxz. Therefore, even if the optical film of the present invention is comparatively thin, the film has a desired retardation value in the thickness direction.

An image display device having such an optical film is excellent in viewing angle property, and may be thin and lighter weight.

In addition, with regard to diethynylfluorene of the present invention, two benzene rings of the main chain portion are bonded (these benzene rings are two benzene rings bonded by "X" in the formula), so that rigidity and linearity of the main chain is high. The diethynylfluorene is used by being introduced into a proper polymer, for example. The polymer of the present invention into which diethynylfluorene having high rigidity and linearity is introduced may be a comparatively thin optical film exhibiting the flat dispersion by forming the polymer into a film.

BEST MODES FOR CARRYING OUT THE INVENTION

In the present specification, meaning of main terms is as follows.

Term "nx" denotes a refractive index in a direction for a maximum refractive index in a plane of the film (x-axis direction), "ny" denotes a refractive index in a direction orthogonal to the x-axis direction in the plane (y-axis direction), and "nz" denotes a refractive index in a direction orthogonal to the x-axis direction and the y-axis direction (thickness direction). Here, nx≧ny.

Term "Δnxz" denotes a refractive index of the thickness direction of a film with a wavelength of λ (nm) at 25° C. The Δnxz can be calculated by the expression Δnxz=nx−nz.

Term "in-plane retardation value (Re(λ))" denotes a retardation value in the plane of a film with a wavelength of λ (nm) at 25° C. The Re(λ) can be calculated by the expression Re(λ)=(nx−ny)×d when a film thickness is denoted by d (nm).

Term "retardation value (Rth[λ]) in the thickness direction" denotes a retardation value in the thickness direction of a film with a wavelength of λ (nm) at 25° C. The Rth(λ) can be calculated by the expression Rth(λ)=(nx−nz)×d when a film thickness is denoted by d (nm).

Term "polymer" includes a high polymer with a polymerization degree (the total polymerization degree of each unit in the case where the polymer contains plural repeating units) of 20 or more, and a low polymer with a polymerization degree of 2 or more and less than 20 (also called an oligomer).

The inventors of the present invention have found out that a film formed from a polymer having a repeating unit represented by the following general formula (I) has wavelength dispersion of retardation value approaching the flat dispersion in a visible light range with a wavelength of 450 to 750 nm and Δnxz is comparatively large. The present invention provides a thin optical film exhibiting the flat dispersion (namely, exhibiting small wavelength dependence of retardation value) by exclusively utilizing the properties of this polymer.

[chemical formula 3]

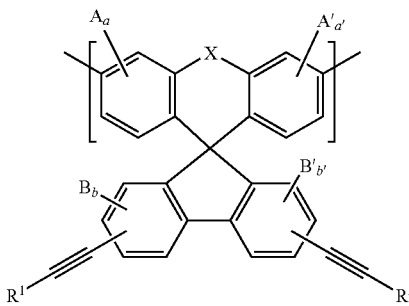

(I)

In the formula (I), A, A', B, and B' each denote a substituent, a and a' denote the number of substituents of the corresponding A and A', and b and b' denote the number of substituents of the corresponding B and B'. The a and a' are integers of 0 to 3 and the b and b' are integers of 0 to 3.

A, A', B and B' each independently denote a halogen or an alkyl group having 1 to 4 carbon atoms. $R^1$ and $R^2$ each independently denote an atom or a group selected from the group consisting of hydrogen, a halogen, an alkyl group having 1 to 10 carbon atoms, a substituted or unsubstituted aryl group, a substituted or unsubstituted vinyl group, a substituted or unsubstituted ethynyl group, an $SiR^3R^4R^5$ group, and a $CR^6R^7(OH)$ group. The $R^3$, $R^4$, and $R^5$ each independently denote an alkyl group having 1 to 6 carbon atoms or an aryl group. The $R^6$ and $R^7$ each independently denote an alkyl group having 1 to 4 carbon atoms.

In the formula (I), X denotes $-CR^8_2-$, $-SiR^9_2-$, $-O-$, $-NR^{10}-$, $-CO-$, or $-SO_2-$. The $R^8$ denotes hydrogen, an alkyl group having 1 to 4 carbon atoms, a perfluoro group, or a substituted or unsubstituted aryl group. The $R^9$ denotes hydrogen, an alkyl group having 1 to 4 carbon atoms, or a substituted or unsubstituted aryl group. The $R^{10}$ denotes hydrogen, an alkyl group having 1 to 4 carbon atoms, or a substituted or unsubstituted aryl group.

In the repeating unit represented by the above-mentioned formula (I), the repeating unit represented by the following formula (II) is preferable.

[chemical formula 4]

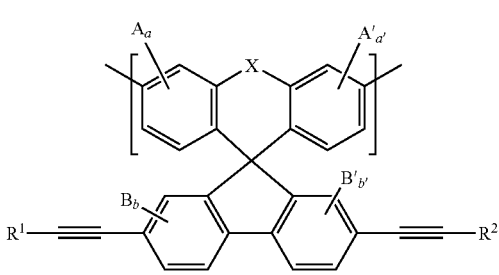

(II)

In the formula (II), A, A', B, B', a, a', b, b', R', $R^2$, and X are the same as in the formula (I).

In the formula (I) and the formula (II), A, A', B, and B' do not particularly influence on wavelength dispersibility of an optical film. Thus, a polymer having a repeating unit in which the above-mentioned A, A', B, and B' are a halogen or an alkyl group having 1 to 4 carbon atoms may be formed into an optical film exhibiting the flat dispersion.

It is preferable that at least one of the above-mentioned A and A' is an alkyl group having 1 to 4 carbon atoms (preferably a methyl group), and the number of substituents thereof is 1 or 2 (a=1 to 2 and a'=1 to 2). A polymer having such a repeating unit is excellent in transparency and solvent solubility.

More preferably, A and A' in the formula (I) and the formula (II) are not substituted (a=0 and a'=0). Further preferably, the B and B' in the formula (I) and the formula (II) are not substituted (b=0 and b'=0).

Further, X in the formula (I) and the formula (II) is preferably $-O-$, $-CO-$, or, $-SO_2-$. The X is more preferably $-O-$.

With regard to the polymer having the repeating unit represented by the above-mentioned formula (I) or the formula (II), two benzene rings of the main chain portion are bonded by a divalent linking group X. Thus, linearity and rigidity of the main chain of the polymer becomes high. Therefore, a film obtained by forming the polymer into a film has comparatively high Δnxz.

It is preferable that the $R^1$ and $R^2$ of the formula (I) and the formula (II) each independently are hydrogen, an alkyl group having 1 to 6 carbon atoms, a trimethylsilyl group, or a $C(CH_3)_2(OH)$ group. More preferably, in the formula (I) and the formula (II), the $R^1$ and $R^2$ each independently are an alkyl group having 1 to 6 carbon atoms, a trimethylsilyl group, or a $C(CH_3)_2(OH)$ group.

In the polymer having the repeating unit represented by the above-mentioned formula (I) or the formula (II), the conjugated system of a fluorene skeleton is extended by a triple bond group (ethynyl group), and the fluorene skeleton is aligned in an approximately orthogonal direction to an extending direction of the main chain. Thus, with regard to this polymer, wavelength dispersibility of retardation value becomes large in a region having the above-mentioned repeating unit. Accordingly, the more the repeating unit represented by the formula (I) or the formula (II) are introduced, the more the wavelength dispersion of retardation value of an obtained film tends to shift from the flat dispersion to the reverse dispersion.

The introduction amount of the repeating unit represented by the above-mentioned formula (I) or the formula (II) is not particularly limited but 1% by mol or more of the whole polymer may be contained. However, as described above, the more the repeating unit represented by the formula (I) or the formula (II) is introduced, the more an obtained optical film approaches the reverse dispersion. For this reason, the polymer preferably contains 5% by mol or more of the repeating unit represented by the formula (I) or the formula (II), more preferably 10% by mol or more, and particularly preferably 12.5% by mol or more of the whole polymer.

On the other hand, excessively large introduction amount of the repeating unit represented by the formula (I) or the formula (II) brings a possibility of not giving an optical film excellent in heat resistance and transparency. For this reason, the upper limit of the introduction amount of the repeating unit represented by the above-mentioned formula (I) or the formula (II) is preferably 90% by mol, more preferably 60% by mol, and particularly preferably 40% by mol.

The repeating unit of the above-mentioned formula (I) or (II) is introduced as a constitutional unit of a proper polymer. Preferably, the repeating unit of the above-mentioned formula (I) or (II) is introduced into a polymer capable of composing a film exhibiting the normal dispersion in forming the polymer into a film (hereinafter, this polymer is occasionally called a "normal dispersion polymer"). The polymer of the present invention, in which the repeating unit of the above-mentioned formula (I) or (II) is introduced into the normal dispersion polymer, may be formed into an optical film exhibiting the flat dispersion in forming the polymer into a film.

The array of the repeating unit of the formula (I) or the formula (II) may be random or block.

Examples of the above-mentioned normal dispersion polymer include a polyester-based polymer, a polyimide-based polymer, a polyamide-based polymer, and a polyamide-imide-based polymer. Among them, the polymer of the present invention is preferably a polymer in which the repeating unit represented by the formula (I) or the formula (II) is introduced into a polyester-based polymer. A film obtained by forming the polymer into a film is excellent in heat resistance, a refractive index thereof is comparatively high, and the film can be formed by coating method.

Hereinafter, in the case of particularly signifying a polymer in which the repeating unit represented by the formula (I) or the formula (II) is introduced into a polyester-based polymer, the polymer is called a "fluorene-introduced polyester polymer".

The above-mentioned polyester-based polymer is not particularly limited as long as it has ester linkage in the main chain. The polyester-based polymer is preferably an aromatic polyester-based polymer by reason of being excellent in linearity and rigidity.

Examples of the aromatic polyester-based polymer include a polymer having the repeating unit represented by the following general formula (III).

  (III)

In the formula (III), Ar denotes an aromatic ring. In the formula (III), Ar is one aromatic ring selected from the group of aromatic rings represented by the following formula group (IV), for example.

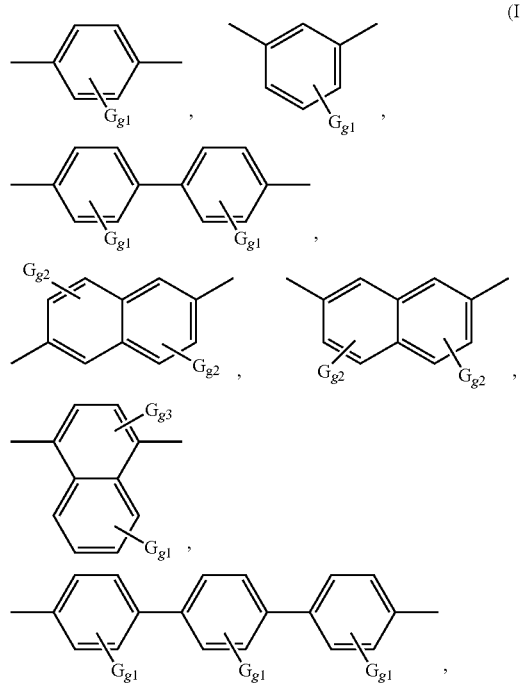 (IV)

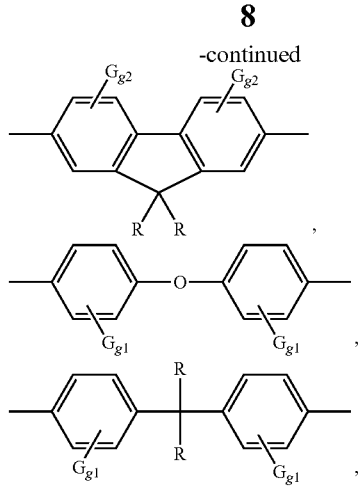

In the formula group (IV), G each independently denote hydrogen, a halogen, an alkyl group having 1 to 4 carbon atoms, or a phenyl group, and g1 to g3 denote the number of substituents thereof. The g1 is an integer of 0 to 4, the g2 is an integer of 0 to 3, and the g3 is an integer of 0 to 2, respectively. R in the formula group (IV) denotes hydrogen or a substituent (this substituent is preferably a halogen, or an alkyl group having 1 to 4 carbon atoms).

Ar of the formula (III) is preferably either of single aromatic rings represented by the following formula group (IV'). G and g1 of the formula group (IV') are the same as in the formula group (IV). An aromatic ring on the left and an aromatic ring on the right represented by the formula group (IV') are called a "p-substitute" and an "m-substitute", respectively.

Ar of the formula (III) is preferably an aromatic ring in which G represented by the formula group (IV) or the formula group (IV') is a hydrogen atom (nonsubstitution). In the case where G is a substituent, the number of substituents thereof is preferably 1 to 2.

[chemical formula 7]

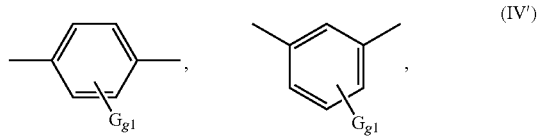 (IV')

In one embodiment of the present invention, the above-mentioned polyester-based polymer more preferably has, in its molecular structure, each of a repeating unit in which Ar of the formula (III) is a p-substitute and a repeating unit in which Ar of the formula (III) is an m-substitute. Such a polymer is high in Δnxz by reason of the introduction of the p-substitute, and is excellent in solvent solubility by reason of the introduction of the m-substitute.

In another embodiment of the present invention, the above-mentioned polyester-based polymer more preferably has a repeating unit in which Ar of the formula (III) is composed only of a p-substitute.

Preferably, the above-mentioned polyester-based polymer further contains the repeating unit represented by the following general formula (V).

[chemical formula 8]

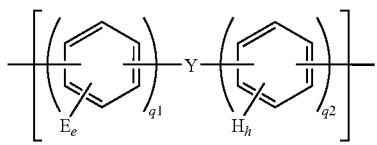

(V)

[chemical formula 9]

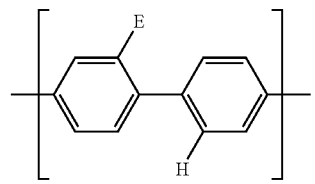

(VI)

In the formula (V), Y denotes a covalent bond, or an atom or a group selected from the group consisting of a $CH_2$ group, a $C(CH_3)_2$ group, a $C(CZ_3)_2$ group (herein, Z is halogen), a CO group, an oxygen atom, an sulfur atom, an $SO_2$ group, an $Si(CH_2CH_3)_2$ group, and an $N(CH_3)$ group. E and H are substituents, e denotes the number of substituents (an integer of 0 to 4) of E, and h denotes the number of substituents (an integer of 0 to 4) of H. E and H denote an atom or a group each independently selected from the group consisting of hydrogen, a halogen, an alkyl group, a substituted alkyl group, a nitro group, a cyano group, a thioalkyl group, an alkoxy group, an aryl group, a substituted aryl group, an alkylester group, and a substituted alkylester group, and when there are a plurality of Es and Hs, each of Es and Hs are the same or different. Also, q1 denotes an integer of 0 to 3 and q2 denotes an integer of 1 to 3. As the halogen, fluorine, chlorine, bromine, or iodine may be cited, for example. As the substituted alkyl group, a halogenated alkyl group may be cited, for example. As the substituted aryl group, a halogenated aryl group may be cited, for example.

Particularly, the repeating unit such that Y in the formula (V) denotes a covalent bond and q1, q2, e, and h denote 1 is preferably used. This repeating unit is represented by the following formula (VI).

In the formula (VI), E and H are each independently denote a atom or a group selected from the group consisting of hydrogen, a halogen, an alkyl group, a substituted alkyl group, a nitro group, a cyano group, a thioalkyl group, an alkoxy group, an aryl group, a substituted aryl group, an alkylester group, and a substituted alkylester group. Preferably, E and H are an atom other than hydrogen or a group, more preferably a substituted alkyl group having 1 to 4 carbon atoms such as halogenated alkyl group (a $CF_3$ and the like) or an alkyl group having 1 to 4 carbon atoms such as $CH_3$.

The fluorene-introduced polyester polymer of the present invention has the repeating unit represented by the above-mentioned formula (I) and/or the formula (II) and the repeating unit represented by the above-mentioned formula (III). Among them, the fluorene-introduced polyester-polymer preferably has the repeating unit represented by the following general formula (VII) or the general formula (VIII).

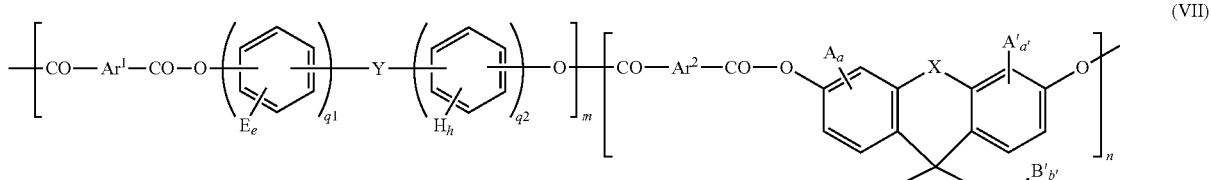

(VII)

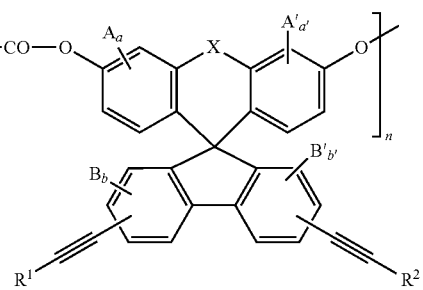

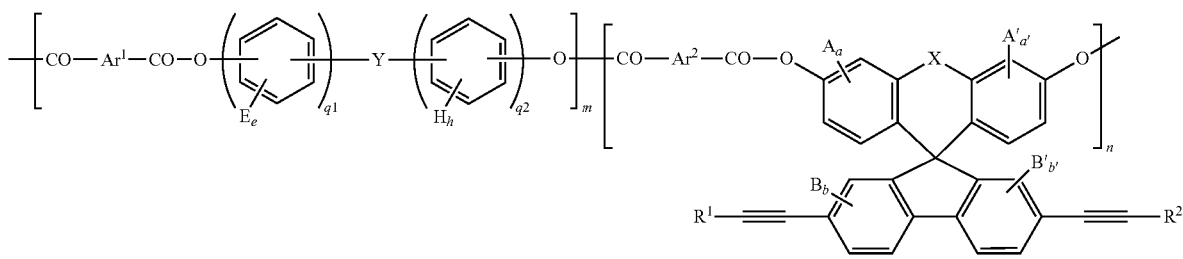

(VIII)

In the formula (VII) and the formula (VIII), A, a, A', a', B, b, B', b', $R^1$, $R^2$, and X are the same as in the formula (I). $Ar^1$ and $Ar^2$ each independently denote an aromatic ring selected from the aromatic ring group represented by the formula group (IV) or the formula group (IV'). In the formula (VII) and the formula (VIII), E, e, H, h, Y, q1, and q2 are the same as in the above-mentioned formula (V). Also, m denotes 1 to 90% by mol and n denotes 10 to 90% by mol. Here, m+n≦100% by mol when the whole polymer is expressed as 100% by mol.

In the formula (VII) and the formula (VIII), A and A' are not substituted preferably (a=0 and a'=0). In the case where A and A' have a substituent, at least one of A and A' is an alkyl group having 1 to 4 carbon atoms (preferably a methyl group), and the number of substituents thereof is preferably 1 or 2 (a=1 to 2 and a'=1 to 2).

In the formula (VII) and the formula (VIII), B and B' are not substituted preferably (b=0 and b'=0).

the p-substitute or the m-substitute, in which G represented by the formula group (IV') is a hydrogen atom (nonsubstitution), is preferable.

The fluorene-introduced polyester polymer only having the p-substitute is represented by the following formula (XI). The fluorene-introduced polyester polymer having the p-substitute and the m-substitute is represented by the following formula (XII).

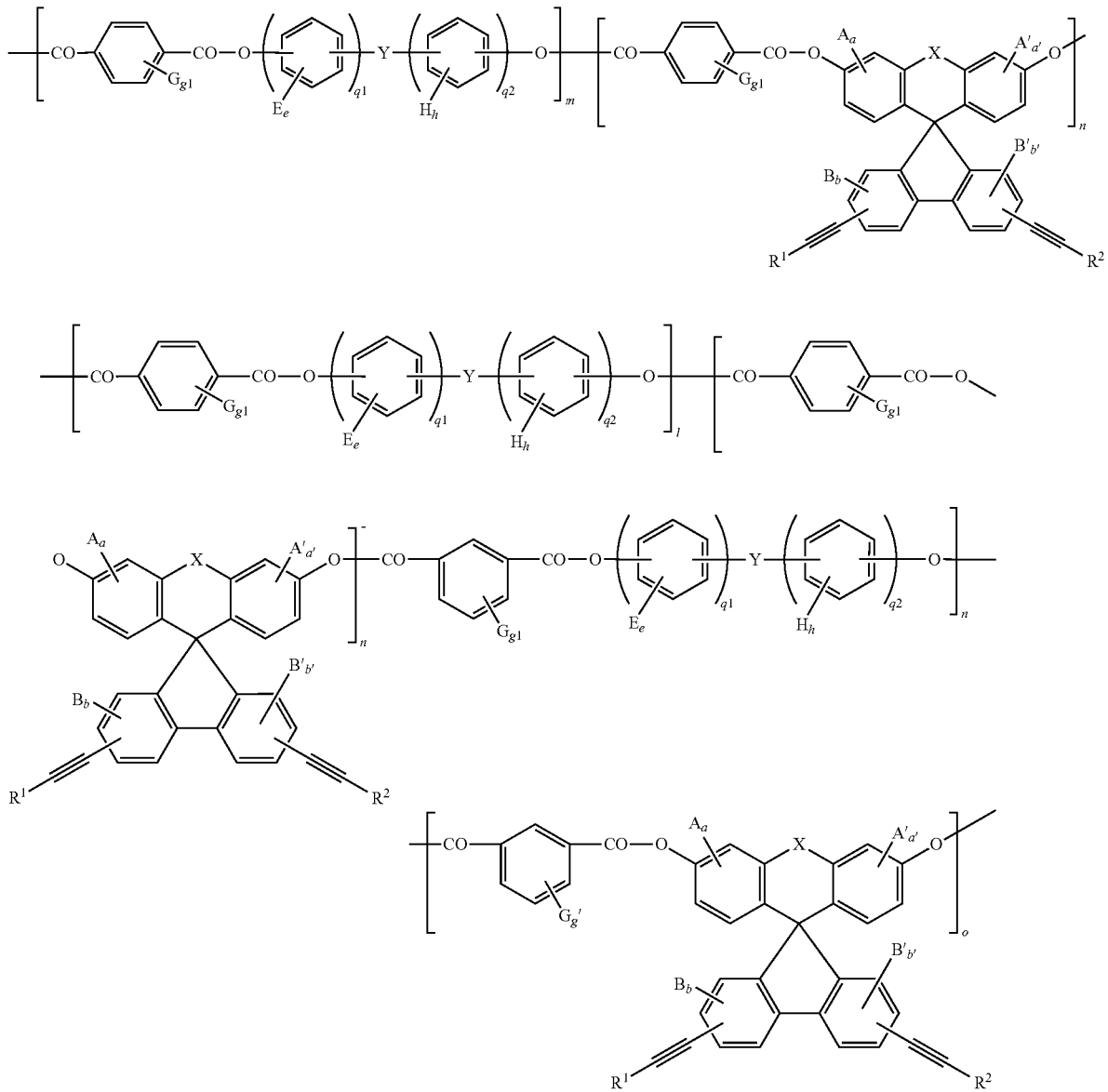

In the formula (VII) and the formula (VIII), X is preferably —O—, —CO, or —SO$_2$—, and more preferably —O—.

Preferably, in the formula (VII) and the formula (VIII), $R^1$ and $R^2$ each independently are hydrogen, an alkyl group having 1 to 6 carbon atoms, a trimethylsilyl group, or a C(CH$_3$)$_2$(OH) group. Particularly preferably, $R^1$ and $R^2$ are each independently an alkyl group having 1 to 6 carbon atoms, a trimethylsilyl group, or a C(CH$_3$)$_2$(OH) group.

Preferably, in the formula (VII) and the formula (VIII), $Ar^1$ and $Ar^2$ are each independently the p-substitute or the m-substitute represented by the formula group (IV'). Particularly, In the formula (XI) and the formula (XII), A, a, A', a', B, b, B', b', $R^1$, $R^2$, and X are the same as in the formula (VII). E, e, H, h, Y, q1, and q2 are the same as in the formula (V), and G and g1 are the same as in the formula group (IV'). In the formula (XI), m denotes 1 to 90% by mol, and n denotes 10 to 90% by mol, respectively. Here, 50% by mol≦m+n≦100% by mol when the whole polymer is expressed as 100% by mol. In the formula (XII), l denotes 1 to 30% by mol, m denotes 1 to 30% by mol, n denotes 1 to 30% by mol, and o denotes 1 to 30% by mol, respectively. Here, 70% by mol≦l+m+n+o≦100% by mol when the whole polymer is expressed as 100% by mol.

The weight-average molecular weight (Mw) of the polymer of the present invention is not particularly limited, but preferably in the range of 1,000 to 1,000,000, and more preferably 2,000 to 500,000. The reason therefor is that when the polymer, in which the weight-average molecular weight thereof is within the above-mentioned range, is shaped into a film, favorable solubility in a solvent is obtained, and cracks due to expansion and contraction and distortion are caused with difficulty.

Also, a glass transition temperature of the polymer of the present invention may be set arbitrary by adjusting type of the substitution, the number of substitutions, type of the main chain, and the introduction amount of the each repeating unit in the formula (I) or the formula (II). The glass transition temperature of the polymer of the present invention is preferably 100° C. or more, and more preferably 130° C. or more. The film obtained by forming the polymer having the glass transition temperature in the above range has sufficient heat resistance as an optical film. The glass transition temperature can be determined by a DSC method according to JIS K 7121(1987).

The polymer having the repeating unit represented by the above-mentioned formula (I) or the formula (II) can be obtained by introducing diethynylfluorene (monomer) represented by the following general formula (X) into a positive dispersion polymer.

[chemical formula 14]

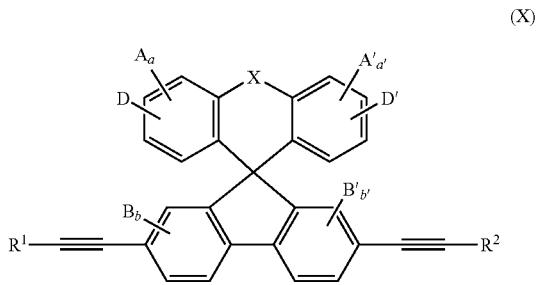

(X)

In the formula (X), A, A', B, and B' each denote a substituent, a and a' denote the number of substituents of the corresponding A and A', and b and b' denote the number of substituents of the corresponding B and B'. The a and a' are an integer of 0 to 3, and the b and b' are an integer of 0 to 3.

A, A', B, and B' each independently denote a halogen or an alkyl group having 1 to 4 carbon atoms. D and D' each independently denote an OH group, an NHR group (R denotes hydrogen or an alkyl group having 1 to 4 carbon atoms), a COOH group, or an NCO group. $R^1$ and $R^2$ each independently denote hydrogen, a halogen, or a group selected from the group consisting of an alkyl group having 1 to 10 carbon atoms, a substituted or unsubstituted aryl group, a substituted or unsubstituted vinyl group, a substituted or unsubstituted ethynyl group, an $SiR^3R^4R^5$ group, and a $CR^6R^7(OH)$ group. $R^3$, $R^4$, and $R^5$ each independently denote an alkyl group having 1 to 6 carbon atoms or an aryl group. $R^6$ and $R^7$ each independently denote an alkyl group having 1 to 4 carbon atoms.

In the formula (X), X denotes —$CR^8_2$—, —$SiR^9_2$—, —O—, —$NR^{10}$—, —CO—, or —$SO_2$—. $R^8$ denotes hydrogen, an alkyl group having 1 to 4 carbon atoms, a perfluoro group, or a substituted or unsubstituted aryl group. $R^9$ denotes hydrogen, an alkyl group having 1 to 4 carbon atoms, or a substituted or unsubstituted aryl group. $R^{10}$ denotes hydrogen, an alkyl group having 1 to 4 carbon atoms, or a substituted or unsubstituted aryl group.

D and D' of the above-mentioned formula (X) are groups bonding to another repeating unit composing a polymer. With regard to diethynylfluorene of the present invention, D and D' of the above-mentioned formula (X) are preferably an OH group or a COOH group, and D and D' are more preferably an OH group. The reason therefor is that such diethynylfluorene may react with carboxylic acid or a hydroxyl group to easily form ester linkage.

The diethynylfluorene represented by the above-mentioned formula (X) is introduced into a polymer as a repeating unit, for example. By introducing the diethynylfluorene of the present invention into a normal dispersion polymer, the optical property of the normal dispersion polymer is improved. Therefore, a film obtained by forming the polymer into a film approaches the flat dispersion. The diethynylfluorene itself of the present invention exhibits the reverse dispersion and the diethynylfluorene has the function of approximating the wavelength dispersion of the normal dispersion polymer to the flat dispersion by being introduced into the polymer.

This function corresponds to the introduction amount of the diethynylfluorene and the obtained film approaches the flat dispersion according as the introduction amount is increased.

Accordingly, the present invention provides a retardation adjustment method of an optical film for adjusting the retardation value of an optical film containing a normal dispersion polymer by introducing the diethynylfluorene represented by the above-mentioned formula (X) into a normal dispersion polymer such as a polyester-based polymer. According to such an adjustment method, the adjustment of the introduction amount of diethynylfluorene into the normal dispersion polymer allows an optional optical film to be produced ranging from an optical film close to the flat dispersion to an optical film exhibiting the flat dispersion.

Diethynylfluorene represented by the above-mentioned formula (X) may be produced by the following method, for example (refer to the following reaction formulae (a) to (c)). However, in the following reaction formulae (a) to (c), A, a, B, b, $R^1$, and $R^2$ are the same as in the formula (X).

(1) Method for Producing Diethynylfluorene in Which D and D' of the Formula (X) are an OH Group (Refer to the Reaction Formula (a))

A 2,7-dibromofluorene derivative is reacted with a phenol derivative under an acid catalyst and thereafter reacted with an ethynyl compound under a palladium (0) catalyst.

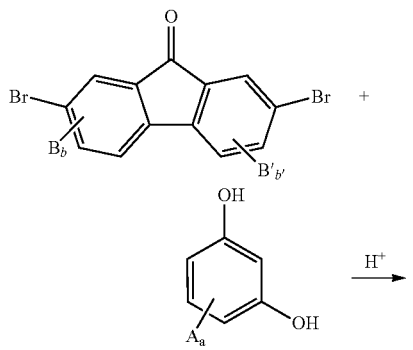

(a)

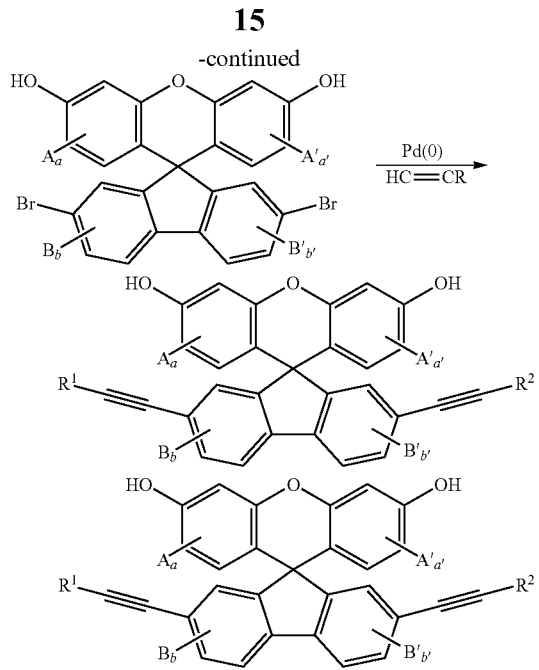

(2) Method for Producing Diethynylfluorene in Which D and D' of the Formula (X) are a COOH Group (Refer to the Following Reaction Formula (b))

A 2,7-dibromofluorene derivative is reacted with a phenol derivative under an acid catalyst, thereafter oxidized with potassium permanganate and protected with an ester. Thereafter, the product is reacted with an ethynyl compound under a palladium (0) catalyst and hydrolyzed.

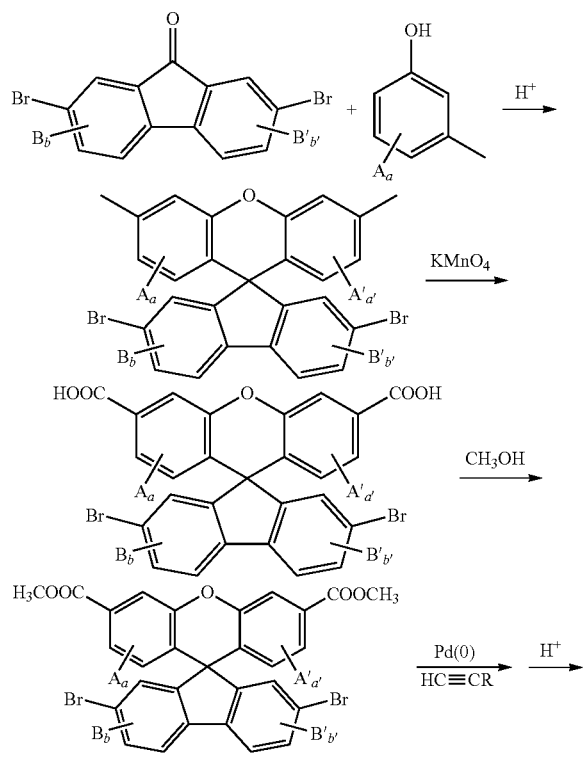

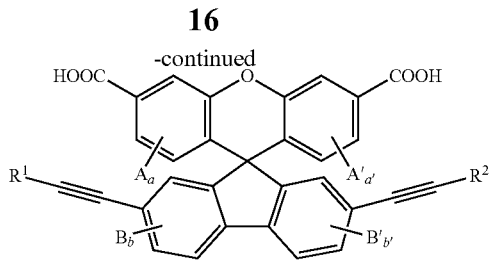

(3) Method for Producing Diethynylfluorene in Which D and D' of the Formula (X) are an NCO Group or an $NH_2$ Group (Refer to the Following Reaction Formula (c))

Diethynylfluorene having a COOH group obtained by the above-mentioned method (2) is reacted with thionyl chloride and thereafter reacted with sodium azide, so that diethynylfluorene having an NCO group may be obtained.

In addition, this is hydrolyzed, so that diethynylfluorene having an $NH_2$ group may be obtained.

The optical film of the present invention can be obtained by forming a forming material containing the polymer of the present invention into a film.

As for the forming material of the optical film, other polymer having different constitution may be added to the forming material in addition to the polymer of the present invention. The other polymer is added as far as an aligning property of the polymer of the present invention is not deteriorated markedly.

As examples of other polymer, for example, various general-purpose resins, engineering plastics, thermoplastic resins, and thermosetting resins may be cited. As the general-purpose resins, for example, polyethylene, polypropylene, polystyrene, polymethyl methacrylate, acrylonitrile-butadiene-styrene resins, acrylonitrile-styrene resins may be cited. As the engineering plastics, for example, polyacetal, polycarbonate, polyamide (nylon), polyethylene terephthalate, and polybutylene terephthalate may be cited. As the thermoplastic resins, for example, polyphenylene sulfide, polyethersulfone, polyketone, polyimide, polycyclohexane dimethanol terephthalate, polyarylate, and liquid crystal polymers may be cited. As the thermosetting resins, for example, epoxy resins and phenol novolac resins may be cited. A blending quantity of these other polymers is, for example, 0 to 50% by mass, and preferably 0 to 30% by mass in the forming material.

Also, the forming material may be added various kinds of additives such as a stabilizer, a plasticizer, and metals, as required.

The thickness of the optical film of the present invention is not particularly limited, but generally 200 μm or less. The thickness of the optical film is preferably 20 μm or less, more preferably 15 μm or less, and particularly preferably 10 μm or less for the reason that an image display device may be thinned. On the other hand, lower limit of the thickness of the optical film may be set arbitrary corresponding to a desired retardation value. The thickness of the optical film is generally 1 μm or more, and preferably 2 μm or more. The polymer of the present invention may be formed into a film by coating. Accordingly, an optical film containing the polymer of the present invention may be formed thin comparatively.

The producing method for the optical film of the present invention is not particularly limited and, for example, the optical film may be produced by forming the forming material containing the polymer of the present invention into a film and drawing (or contracting) as required. The film-forming may be conducted by coating the forming material on a proper base material.

Examples of the coating method for the above-mentioned forming material include a method for coating the forming material on a base material by heating to melt, a method for coating polymer solution in which the forming material is dissolved in a solvent on a base material and the like. The above-mentioned method for coating polymer solution on a base material is preferable in view of production efficiency, molecular alignment control, and optical anisotropy control.

In particular, a coating film exhibiting negative uniaxial (nx≅ny>nz) may be formed by coating the polymer solution containing the polymer of the present invention on a base material.

Specifically, the polymer solution containing the polymer of the present invention is coated on a base material, and thereafter shrinkage force is applied in a plane of the coating film (the x-axis direction and the y-axis direction) in the process of drying, and then a coating film exhibiting negative uniaxial may be formed. Thus, the polymer of the present invention may be formed into a coating film exhibiting optical uniaxial by being coated on a base material regardless of the presence or absence of the alignment of the base material.

Here, "nx≅ny" includes a case in which nx and ny are substantially identical in addition to a case in which nx and ny are completely identical. The case in which nx and ny are substantially identical refers, for example, to a case in which an Re(590) is 0 nm to 10 nm, and preferably 0 nm to 5 nm.

The polymer solution may be prepared by dissolving the polymer of the present invention (other polymer and various kinds of additives may be blended, as required) in a proper solvent. The polymer of the present invention is excellent in solvent solubility, so that the polymer solution may be prepared easily.

The solvent is not particularly limited as far as the solvent can dissolve the polymer of the present invention and arbitrary selected. As example of the solvent, an organic solvent may be cited, for example. As the organic solvent, halogenated hydrocarbons such as chloroform, dichloromethane, carbon tetrachloride, dichloroethane, tetrachloroethane, trichloroethylene, tetrachloroethylene, chlorobenzene, and ortho-dichlorobenzene; phenols such as phenol and para-chlorophenol; aromatic hydrocarbons such as benzene, toluene, xylene, methoxybenzene, and 1,2-dimethoxybenzene; ketones such as acetone, methyl ethyl ketone, methyl isobutyl ketone, cyclohexanone, cyclopentanone, 2-pyrrolidone, and N-methyl-2-pyrrolidone; esters such as ethyl acetate and butyl acetate; alcohols such as t-butyl alcohol, glycerin, ethylene glycol, triethylene glycol, ethylene glycol monomethyl ether, diethylene glycol dimethyl ether, propylene glycol, dipropylene glycol, and 2-methyl-2,4-pentanediol; amides such as dimethylformamide and dimethylacetoamide; nitrile-based solvents such as acetonitrile and butyronitrile; ethers such as diethyl ether, dibutyl ether, and tetrahydrofurane; carbon disulfide; cellosolves such as ethylcellosolve and butylcellosolve; and the like may be cited. These solvents may be used alone or in the form of a mixture of two or more thereof.

With regard to the polymer solution, solids such as a polymer is preferably blended in the range of 5 to 50 parts by mass, and more preferably 10 to 40 parts by mass with respect to 100 parts by mass of the solvent. The polymer solution in the above range has appropriate viscosity for coating.

Also, as a coating method of the polymer solution, a spin coating method, a roll coating method, a flow coating method, a print method, a dip coating method, a coating film-forming method, a bar coating method, a gravure printing method, and the like may be cited.

The coating film on a base material may be dried after forming the coating film by coating the polymer solution. The drying is performed by natural drying, air drying, drying by heating, and the like, for example. When the drying by heating is adopted, heating temperature is not particularly limited, but 25 to 250° C., and preferably 40 to 200° C., for example.

The solvent amount remaining in the coating film finally obtained (namely, an optical film) is preferably 1% by mass or less, more preferably 0.5% by mass or less. The reason therefor is that an optical film with a small remaining solvent amount is so excellent in dimensional stability that the change of optical property with time is caused with difficulty.

The base material to be coated with the above-mentioned forming material (the polymer solution and the like) is not particularly limited. The base material may be a base material made of a synthetic resin or a base material made of an inorganic compound such as a glass base material and a silicon wafer. As examples of the base material made of a synthetic resin, a film produced by the cast method, a film produced in such a manner that a melted polymer is formed into a film and thereafter subjected to drawing treatment, and the like may be cited. Among them, a film in which drawing treatment is performed is preferable, for the reason that the forming material can be coated accurately.

Further, the base material excellent in transparency is preferably used. The use of the base material excellent in transparency allows an optical film formed on the base material to be used directly without being peeled off the base material.

As the resin component of the base material made of a synthetic resin, for example, acetate resins such as triacetyl cellulose (TAC), polyester resins, polyethersulfone resins, polysulfone resins, polycarbonate resins, polyamide resins, polyimide resins, polyolefin resins, acrylic resins, polynorbornene resins, cellulose resins, polyarylate resins, polystyrene resins, polyvinyl alcohol resins, polyvinyl chloride resins, polyvinylidene chloride resins, liquid crystal polymers, mixtures thereof, and the like may be cited. Further, a mixture of a thermoplastic resin having a substituted imide group or a non-substituted imide group on the side chain and a thermoplastic resin having a substituted phenyl group or a non-substituted phenyl group and a nitrile group on the side chain may be used as the resin component (this mixture is described in Japanese Unexamined Patent Publication No. 2001-343529).

The thickness of the base material is, for example, 12 μm to 200 μm, preferably 20 μm to 150 μm, and more preferably 25 μm to 100 μm. In the case where the base material has a thickness of 12 μm or more, the polymer solution may be coated further accurately. On the other hand, in the case where the base material has a thickness of 200 μm or less, distortion amount of the optical film may be further restricted.

By coating the forming material containing the polymer of the present invention on the base material, the coating film exhibiting optical uniaxial can be formed. This coating film is an optical film of the present invention. Accordingly, the optical film of the present invention is thin and exhibits optically uniaxial (index ellipsoid thereof exhibits $nx \equiv ny > nz$). The optical film may be used as a retardation film.

An optical film exhibiting optically biaxial (index ellipsoid thereof exhibits $nx > ny > nz$) may be formed by drawing or contracting the above-mentioned coating film.

As a drawing method of the coating film, for example, a free-end longitudinal stretching method of uniaxially stretching in a longitudinal direction of the film and a fixed-end transverse stretching method of uniaxially stretching in a width direction with the film fixed in a longitudinal direction may be preferably cited. Also, a biaxial stretching method of sequential or simultaneous stretching in both a longitudinal direction and a width direction may be cited as the other drawing method, for example. In the case where the base material on which the coating film is formed is a base material which can be drawn, a method for drawing the base material is preferable. According to this drawing method, the base material can be drawn uniformly, thus the coating film can be drawn indirectly and uniformly corresponding to the drawing of the base material. Also, this drawing method is applicable to continuous production process and preferable in terms of improving mass productivity of products. The base material and the coating film may be drawn concurrently.

Further, in the case where the base material on which the coating film is formed is a contractable base material, the contraction of the base material allows the contraction of the coating film to be indirectly performed. On this occasion, the contraction percentage is preferably controlled by utilizing a drawing machine or the like. As examples of the control method, a method for temporarily releasing a clip of a drawing machine to relax the base material in the transfer direction of the base material, a method for gradually narrowing the interval of a clip of a drawing machine, and the like may be cited.

With regard to the optical film of the present invention, the retardation value in the thickness direction ($Rth(\lambda)$) and the in-plane retardation value ($Re(\lambda)$) can be adjusted arbitrary. This adjustment may be performed by selecting constitution and molecular weight of the polymer material which is used for, setting thickness, and setting a drawing (or construction) ratio of the optical film, for example.

With regard to the optical film containing the polymer of the present invention, the wavelength dispersion thereof approaches the flat dispersion. Specifically, the optical film of the present invention satisfies a relation ship of $0.97 \leq Rth(450)/Rth(550) \leq 1.06$ and $1.03 \geq Rth(650)/Rth(550) \geq 95$.

Particularly, the optical film containing the polymer that the introduction amount of the formula (I) or the formula (II) is increased, or the optical film containing the polymer that a proper substitution is selected as $R^1$ and $R^2$ of the formula (I) or the formula (II), satisfies a relationship of $0.97 \leq Rth(450)/Rth(550) \leq 1.03$ and $0.97 \leq Rth(450)/Rth(550) \leq 1.02$. The wavelength dispersion of this optical film further approaches the flat dispersion.

Also, the optical film containing the polymer that the introduction amount of the formula (I) or the formula (II) is increased, or the optical film containing the polymer that a proper substitution is selected as $R^1$ and $R^2$ of the formula (I) or the formula (II), satisfies a relationship of $1.03 \geq Rth(650)/Rth(550) \geq 97$ and $1.03 \geq Rth(650)/Rth(550) \geq 98$. This optical film further approaches the flat dispersion as same as above.

In the case where the index ellipsoid of the optical film of the present invention satisfies a relationship of $nx > ny > nz$, the in-plane retardation value of the optical film satisfies a relationship of $Re(450)/Re(550) < 1.06$ and $Re(650)/Re(550) \geq 95$. As for the optical film containing the polymer in which the introduction amount of the formula (I) is increased, the wavelength dispersion of in-plane retardation value thereof further approaches the flat dispersion.

Here, $Rth(450)$, $Rth(550)$, and $Rth(650)$ denote a retardation value in the thickness direction with a wavelength of 450 nm, 550 nm, and 650 nm at 25° C. $Re(450)$, $Re(550)$, and $Re(650)$ denote an in-plane retardation value with a wavelength of 450 nm, 550 nm, and 650 nm at 25° C.

The refractive index of the optical film of the present invention can be set appropriately by the introduction amount of the formula (I) or the formula (II), constitution of polyester, and the like. The refractive index ($\Delta nxz(550)$) of the optical film of the present invention with a wavelength of 550 nm is preferably 0.005 or more, and more preferably 0.01 or more. The upper limit of the $\Delta nxz(550)$ is preferably 0.070.

The optical film of the present invention may be used for arbitrary appropriate applications. As typical applications of the optical film of the present invention is a retardation film. The retardation film is used as a $\lambda/4$ plate, a $\lambda/2$ plate, and a viewing angle expansion film which are used for a liquid crystal display. As other applications of the optical film, an antireflection film mounted on an image display device is cited. As the image display device, a liquid crystal display, an organic light emitting display, a plasma display, and the like may be cited.

The optical film of the present invention can be used as form of an optical laminated body in which other optical member is laminated. As the optical laminated body, for example, a laminated body (this laminated body is typically called as a polarizing plate) in which the optical film of the present invention and a polarizer having a protective layer are laminated, and a laminated body in which the optical film of the present invention and other retardation film are laminated may be cited.

The optical film and the like which compose these laminated bodies are generally adhered by well-known adhesives (or pressure sensitive adhesives). As the adhesives, for example, a solvent adhesive, an emulsion adhesive, a pressure sensitive adhesive, a rewet adhesive, a polycondensation adhesive, a solventless adhesive, a film form adhesive, a hot-melt adhesive, and the like may be cited.

The polarizer is an optical element which can convert a natural light or a polarized light into a linear polarized light. The polarizer is not particularly limited and proper and appropriate one is adopted. As the polarizer, a drawn film containing a vinyl alcohol-based polymer including iodine or a dichroic dye as a main component is preferable. The thickness of the polarizer is generally 5 μm to 50 μm. The protective layer is adhered to the polarizer for preventing constriction or expansion of the polarizer. As the protective layer, a polymer film containing a cellulose-based polymer or a norbornene-based polymer is cited. The thickness of the protective layer is generally 10 μm to 200 μm. The protective layer may combine with a base material when the optical film of the present invention is formed.

The image display device of the present invention has the optical film of the present invention.

The image display device of the present invention may be constructed same as the conventional image display device except that the optical film of the present invention is mounted on the liquid crystal panel.

The image display device of the present invention is used for proper and appropriate applications. When the image display device is a liquid crystal display, for example, office automation equipments such as a personal computer monitor, a notebook computer, and a copying machine; portable equipments such as a portable telephone, a watch, a digital camera, a personal digital assistant (PDA), and a portable game machine; domestic electrical equipments such as a video camera and a microwave oven; on-vehicle equipments such as a back monitor, a monitor for a car navigation system, and a car audio; display equipments such as an information monitor for a commercial store; security equipments such as an observation monitor; and care/medical equipments such as a care monitor and a medical monitor may be cited as applications.

The image display device of the present invention includes a liquid crystal display, an organic light emitting display, a plasma display, and the like. The preferable application of the image display device is a TV set. The screen size of the TV set is preferably wide 17 type (373 mm×224 mm) or more, more preferably wide 23 type (499 mm×300 mm) or more, and particularly preferably wide 32 type (687 mm×412 mm) or more.

The polymer of the present invention is appropriate as a forming material for various kinds of optical films, for the reason that the polymer is excellent in transparency and heat resistance, and exhibits predetermined retardation.

Further, the polymer of the present invention may be used as the forming material for various kinds of optical members such as a plastic lens, a prism, an optical disc, an optical fiber, a photoresist, and a hologram, except for an optical film.

Also, the polymer of the present invention may be used for such as an electrolyte film for a fuel cell, a coating material for a semiconductor (such as a chip surface protective material, a chip interlayer insulating material, and the like), a sealing material for a semiconductor device, a material for a flexible circuit board, a material for a photo-alignment film, an optical waveguide material, a cosmic ray-proof material (usable for an artificial satellite or the like), a material for a separation film (for gas separation or the like), a resist material, and a material for a printer (a toner transfer belt for a color printer or the like).

In addition, the polymer of the present invention may be used as a coating agent for protecting a member surface, for the reason that the polymer is excellent in solvent solubility.

EXAMPLES

Next, the present invention is described in detail with reference to Examples and Comparative Example of the present invention. However, the present invention is not limited to the following Examples.

Each analytical method used in Examples and Comparative Example is as follows.

(1) Identification of Chemical Constitution:

The chemical constitution was identified by using a nuclear magnetic resonance spectrometer [product name "AVANCEII300", manufacture by Bruker Japan Co., Ltd.] (measurement solvent; deuterated chloroform or deuterated DMSO, frequency; 300 MHz, observation nucleus; $^1H$, $^{13}C$, measured temperature; 25° C.).

(2) Measurement of Weight-Average Molecular Weight:

Each sample was prepared to 0.1%-DMF solution and filtered through a 0.45-μm membrane filter to thereafter measure weight-average molecular weight by using a GPC itself ("HLC-8120GPC", manufactured by Tosoh Corporation) in which a detector (RI) is incorporated. Specifically, the column temperature was 40° C. and the pump flow rate was 0.40 mL/minute, and the molecular weight of measuring samples was calculated as the molecular weight converted into polyethylene oxide by using the calibration curve of standard polyethylene oxide with the molecular weight thereof known previously. The used column was such that super AWM-H (diameter 6.0 mm×15 cm), super AW4000 (diameter 6.0 mm×15 cm), and super AW2500 (diameter 6.0 mm×15 cm) were connected in series. The used mobile phase was such that 10 mmol LiBr and 10 mmol phosphoric acid were put in a measuring flask to add DMF thereto and determine the total amount at 1 L.

(3) Measurement of Thickness:

The thickness was measured by using a trade name of "Dektak" manufactured by SLOAN.

(4) Measurement of Δnxz and Rth(λ):

The measurement of Δnxz and the like was performed at a temperature of 23° C. and a wavelength of λ by using a trade name of "KOBRA-WPR" manufactured by Oji Scientific Instruments. Rth(λ) was calculated in such a manner that light with a wavelength of λ was made to enter at an angle of 40° with the sample normal direction to convert the measured value (R40λ) into Rth(λ).

Synthesis Example 1

Synthesis of 2,7-dihydroxy-9,9-[2,7-bis(2-methyl-2-hydroxy-3-butynyl)fluorenyl]xanthene 30.0 g of 2,7-dibromofluorenone and 24.43 g of resorcinol were dissolved in 100 mL of toluene, and 3.48 g of concentrated sulfuric acid and 0.09 g of mercaptopropionic acid were added thereto and the mixture was heated at 80° C. for 18 hours. After completion of the reaction, the solution was neutralized with sodium hydroxide and chloroform was added thereto, and the precipitated solid was separated by filtration to thereby obtain a bromo derivative.

Next, 0.008 g of bis(triphenylphosphine)dichloropalladium (II) and 0.002 g of copper iodide (I) were dissolved in 1.0 mL of dioxane under a nitrogen atmosphere. 0.005 g of tri(tertiary butyl)phosphine, 0.046 g of di-isopropylamine, 0.037 g of 2-methyl-3-butyne-2-ol, and 0.10 g of the obtained bromo derivative were added to the solution, and the solution was stirred at 80° C. for 24 hours. Thereafter, the solvent was removed under reduced pressure, and the residue was purified in a silica gel packed column with the use of a developing solvent (a mixed solvent of hexane and ethyl acetate). In addition, recrystallization was repeated in a mixed solvent (hexane:chloroform=2:1) to thereby obtain 0.057 g of a compound (yield 56.4%). Through the measurement by NMR, the obtained compound was 2,7-dihydroxy-9,9-[2,7-bis(2-methyl-2-hydroxy-3-butynyl)fluorenyl]xanthene represented by the following formula (1).

(1)

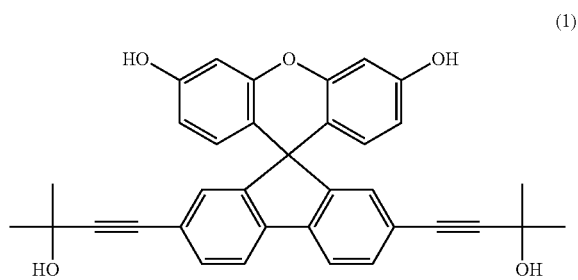 [SMILES: CC(C)(O)C#Cc1ccc2c(c1)C1(c3ccc(O)cc3Oc3cc(O)ccc31)c1cc(C#CC(C)(C)O)ccc1-2]

Synthesis Example 2

Synthesis of 2,7-dihydroxy-9,9-[2,7-bis(5-hexynyl) fluorenyl]xanthene 1.010 g of palladium carbon and 0.365 g of copper iodide (I) were dissolved in 95 mL of dimethylacetamide and 5 mL of water under a nitrogen atmosphere. 0.800 g of triphenylphosphine, 0.046 g of di-isopropylamine, 4.000 g of 1-hexyne, and 10.00 g of the bromo derivative obtained in the above-mentioned <Synthesis Example 1> were added to the solution, and the solution was stirred at 80° C. for 24 hours. Thereafter, the solvent was removed under reduced pressure and the residue was purified in a silica gel packed column with the use of a developing solvent (a mixed solvent of hexane and ethyl acetate). After the purification, 3.370 g of a compound (yield 33.8%) was obtained. Through the measurement by NMR, the obtained compound was 2,7-dihydroxy-9,9-[2,7-bis(5-hexynyl)fluorenyl]xanthene represented by the following formula (2).

(2)

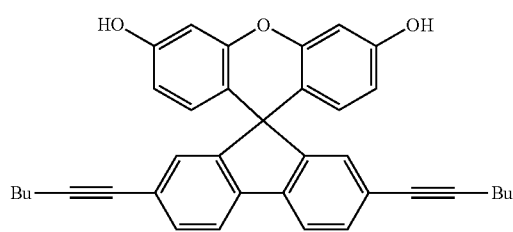

Example 1

4 mL of pyridine was added to 0.52 g of ice-cooled thionyl chloride. 0.17 g of isophthalic acid and 0.17 g of terephthalic acid were dissolved in 4 mL of pyridine, and this solution was slowly added to the above-mentioned pyridine containing the above-mentioned thionyl chloride over 5 to 10 minutes. Thereafter, the cooling bath was removed and the solution was stirred at room temperature for 20 minutes (this mixed solution is called Solution A). On the other hand, 0.34 g of bis(4-hydroxyphenyl)hexafluoropropane and 0.52 g of 2,7-dihydroxy-9,9-[2,7-bis(5-hexynyl)fluorenyl]xanthene obtained in the above-mentioned <Synthesis Example 2> were dissolved in 4 mL of a pyridine solution (this solution is called Solution B). Solution B was added to Solution A at a time, and the mixture was heated at 80° C. for 4 hours and thereafter stirred for one night. The obtained solution was diluted with chloroform and thereafter poured into methanol. The precipitated polymer was refluxed in methanol, filtered off and dried to thereby obtain 0.91 g of a polymer (yield 88.1%). Through the measurement by NMR, this polymer was a fluorene-introduced polyester polymer represented by the following formula (3). The weight-average molecular weight of the polymer was 64,300.

(3)

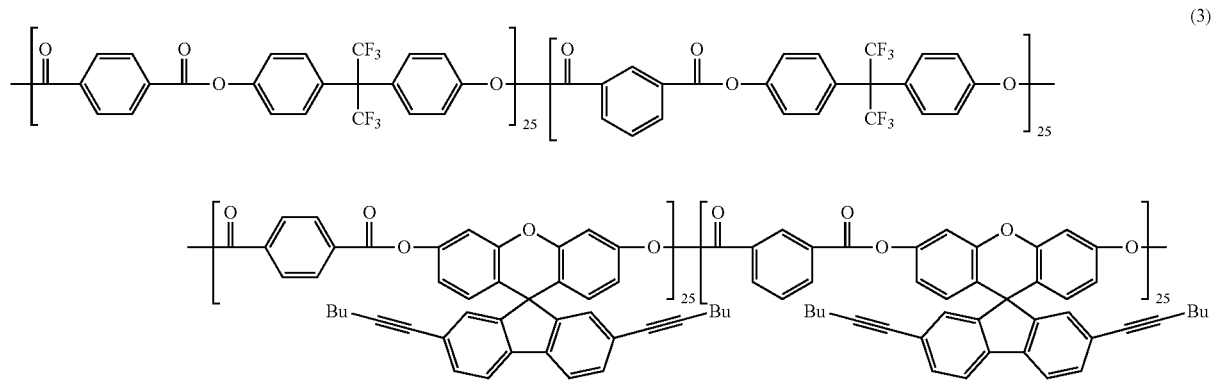

The obtained fluorene-introduced polyester polymer was dissolved in cyclohexanone to prepare a polymer solution (solid concentration 16% by mass). This polymer solution was coated on a glass plate by a spin coat method, dried at 80° C. for 5 minutes and thereafter dried at 150° C. for 30 minutes to thereby produce a polyester film.

The dry thickness of this polyester film was 9.81 μm.

The birefringence index ($\Delta nxz$) of this polyester film at 550 nm was 0.0066.

When the wavelength dispersion of retardation value in the thickness direction of this film was measured, Rth(450)/Rth(550) was 0.98 and Rth(650)/Rth(550) was 1.02.

Example 2

A polymer was synthesized in the same manner as in Example 1 except for replacing 0.34 g of bis(4-hydroxyphenyl)hexafluoropropane of Example 1 with 0.23 g of bisphenol A. Incidentally, through the measurement by NMR, this polymer was a fluorene-introduced polyester polymer represented by the following formula (4). The weight-average molecular weight of the polymer was 17,200.

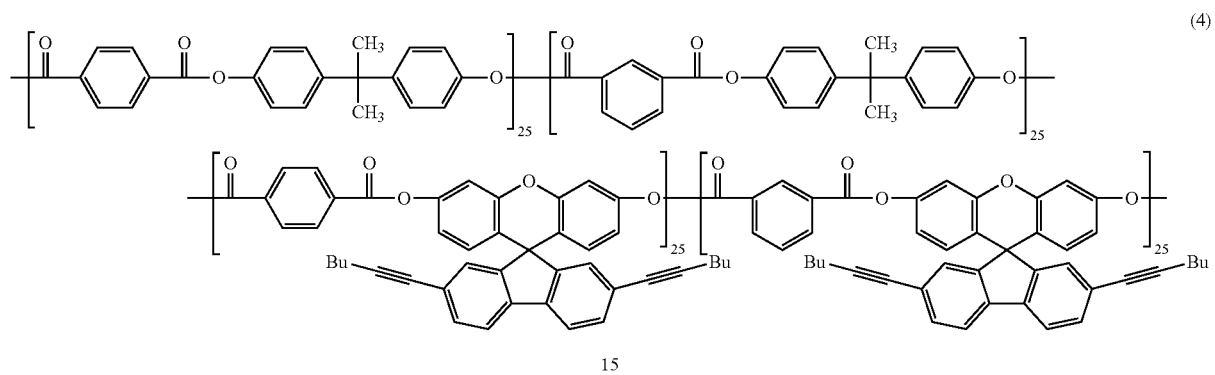

(4)

The obtained fluorene-introduced polyester polymer was formed into a polyester film in the same manner as in Example 1 (dry thickness: 4.36 μm).

The birefringence index (Δnxz) of this polyester film of Example 2 at 550 nm was 0.0067.

With regard to this film, Rth(450)/Rth(550) was 0.98 and Rth(650)/Rth(550) was 1.01.

Example 3

A polymer was synthesized in the same manner as in Example 1 except for replacing 0.34 g of bis(4-hydroxyphenyl)hexafluoropropane of Example 1 with 0.32 g of bis(trifluoromethyl)biphenyl. Incidentally, through the measurement by NMR, this polymer was a fluorene-introduced polyester polymer represented by the following formula (5). The weight-average molecular weight of the polymer was 5,290.

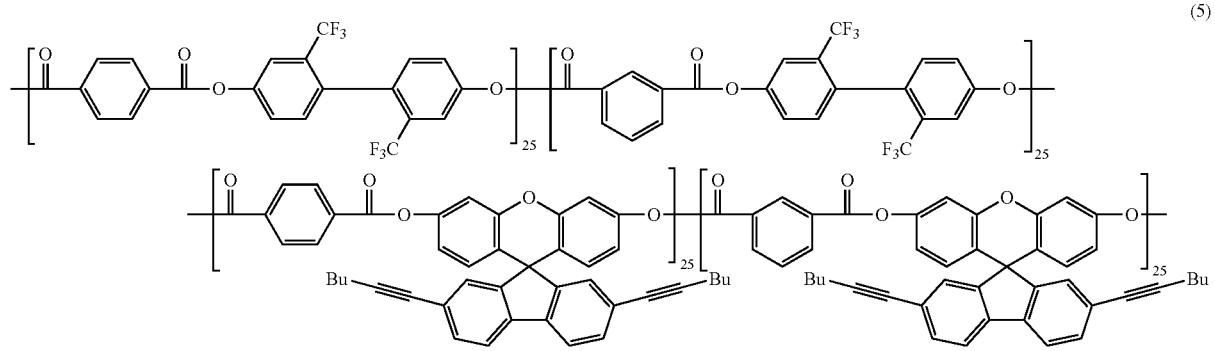

(5)

The obtained fluorene-introduced polyester polymer was formed into a polyester film in the same manner as in Example 1 (dry thickness: 2.40 μm).

The birefringence index (Δnxz) of this polyester film of Example 3 at 550 nm was 0.011.

With regard to this film, Rth(450)/Rth(550) was 1.00 and Rth(650)/Rth(550) was 1.02.

Example 4

A polymer was synthesized in the same manner as in Example 1 except for replacing 0.34 g of bis(4-hydroxyphenyl)hexafluoropropane of Example 1 with 0.21 g of bis(4,4'-dihydroxy-2,2'-dimethyl)biphenyl. Incidentally, through the measurement by NMR, this polymer was a fluorene-introduced polyester polymer represented by the following formula (6). The weight-average molecular weight of the polymer was 13,100.

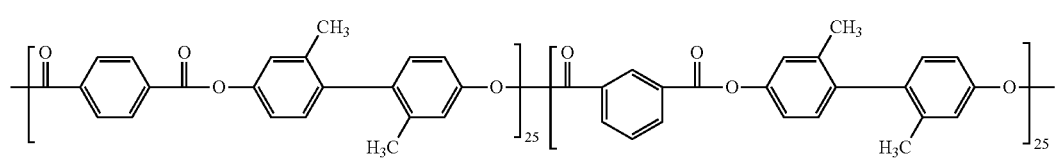

(6)

-continued

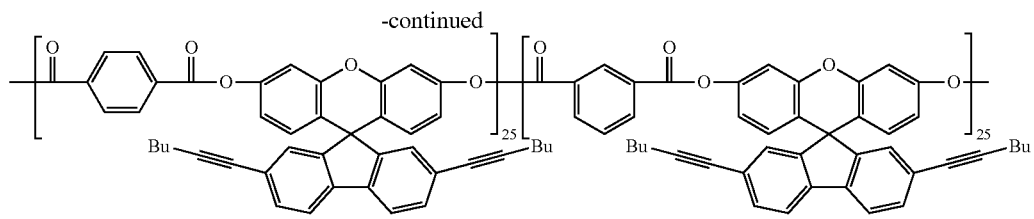

The obtained polymer was formed into a polyester film in the same manner as in Example 1 (dry thickness: 4.35 μm).

The birefringence index (Δnxz) of this polyester film of Example 4 at 550 nm was 0.011.

With regard to this film, Rth(450)/Rth(550) was 1.00 and Rth(650)/Rth(550) was 1.02.

Example 5

A polymer was synthesized in the same manner as in Example 1 except for replacing 0.17 g of isophthalic acid and 0.17 g of terephthalic acid of Example 1 with 0.33 g of terephthalic acid, and replacing 0.34 g of bis(4-hydroxyphenyl)hexafluoropropane of Example 1 with 0.21 g of bis(4,4'-dihydroxy-2,2'-dimethyl)biphenyl. Incidentally, through the measurement by NMR, this polymer was a fluorene-introduced polyester polymer represented by the following formula (7). The weight-average molecular weight of the polymer was 13,000.

(7)

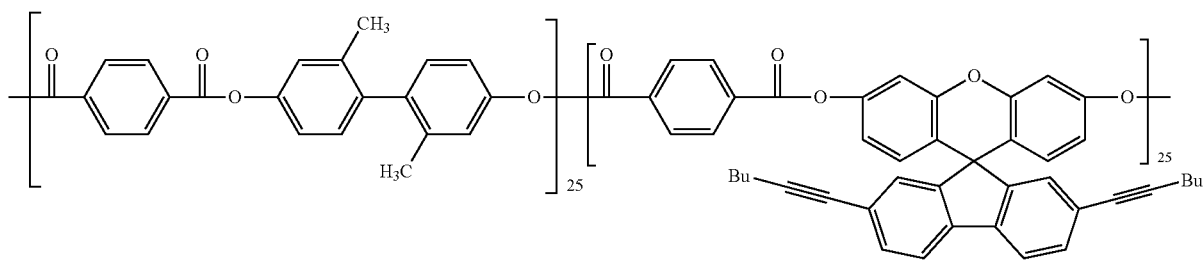

The obtained fluorene-introduced polyester polymer was formed into a polyester film in the same manner as in Example 1 (dry thickness: 4.27 μm).

The birefringence index (Δnxz) of this polyester film of Example 5 at 550 nm was 0.015.

With regard to this film, Rth(450)/Rth(550) was 1.00 and Rth(650)/Rth(550) was 1.02.

Comparative Example 6.77 g of methyl ethyl ketone and 25.88 g of resorcinol were dissolved in 7 mL of toluene. 3.66 g of concentrated sulfuric acid and 0.09 g of mercaptopropionic acid were added to the solution, and the mixture was heated at 90° C. for 21 hours. After completion of the reaction, the solution was neutralized with sodium hydroxide and chloroform was added thereto, and the precipitated solid was separated by filtration. In this manner, 5.00 g of 2,7-dihydroxy-9-ethyl-9-methylxanthene was obtained.

A polymer was synthesized in the same manner as in Example 1 except for replacing 0.34 g of bis(4-hydroxyphenyl)hexafluoropropane of Example 1 with 0.32 g of bis(trifluoromethyl)biphenyl, and replacing 0.52 g of 2,7-dihydroxy-9,9-[2,7-bis(5-hexynyl)fluorenyl]xanthene with 0.26 g of 2,7-dihydroxy-9-ethyl-9-methylxanthene obtained in the above. Incidentally, through the measurement by NMR, this polymer was a polyester-based polymer represented by the following formula (8). The weight-average molecular weight of the polymer was 4,310.

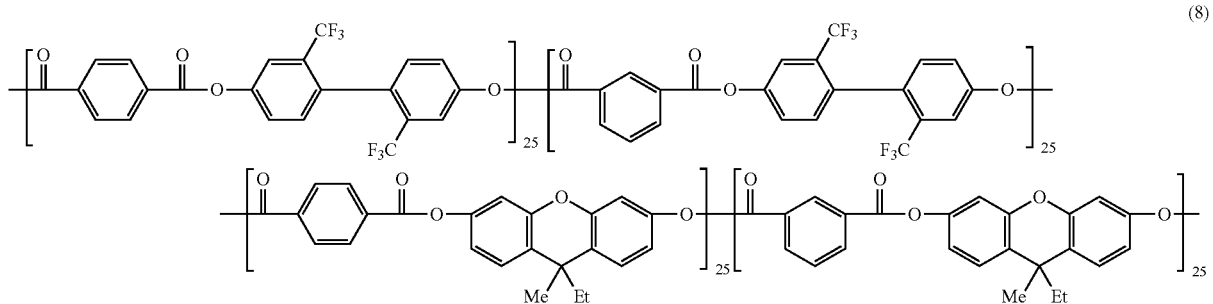
(8)

The obtained polymer was formed into a polyester film in the same manner as in Example 1 (dry thickness: 1.96 μm).

The birefringence index (Δnxz) of this polyester film of Comparative Example at 550 nm was 0.0213.

With regard to this film, Rth(450)/Rth(550) was 1.06 and Rth(650)/Rth(550) was 0.97.

As described above, the optical films of Example 1 to Example 5 exhibited the flat dispersion. On the other hand, Rth(450)/Rth(550) of the optical film of Comparative Example was 1.06, and the film exhibited the normal dispersion.

What is claimed is:

1. A retardation film comprising:
a polymer having a repeating unit represented by the following general formula (I):

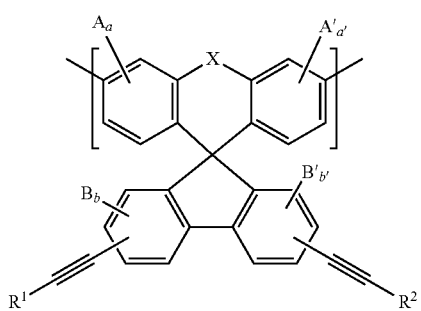
(I)

wherein A, A', B, and B' each denote a substituent, a and a' denote the number of substituents of the corresponding A and A' (an integer of 0 to 3), and b and b' denote the number of substituents of the corresponding B and B' (an integer of 0 to 3); A, A', B and B' each independently denote a halogen or an alkyl group having 1 to 4 carbon atoms; $R^1$ and $R^2$ each independently denote an atom or a group selected from the group consisting of hydrogen, a halogen, an alkyl group having 1 to 10 carbon atoms, a substituted or unsubstituted aryl group, a substituted or unsubstituted vinyl group, a substituted or unsubstituted ethynyl group, an $SiR^3R^4R^5$ group ($R^3$ to $R^5$ each independently denote an alkyl group having 1 to 6 carbon atoms or an aryl group) and a $CR^6R^7(OH)$ group ($R^6$ and $R^7$ each independently denote an alkyl group having 1 to 4 carbon atoms); and X denotes —$CR^8_2$— ($R^8$ denotes hydrogen, an alkyl group having 1 to 4 carbon atoms, a perfluoro group, or a substituted or unsubstituted aryl group), —$SiR^9_2$— ($R^9$ denotes hydrogen, an alkyl group having 1 to 4 carbon atoms, or a substituted or unsubstituted aryl group), —O—, —$NR^{10}$— ($R^{10}$ denotes hydrogen, an alkyl group having 1 to 4 carbon atoms, or a substituted or unsubstituted aryl group), —CO—, or —$SO_2$—.

2. The retardation film according to claim 1, wherein the repeating unit is represented by the following general formula (II):

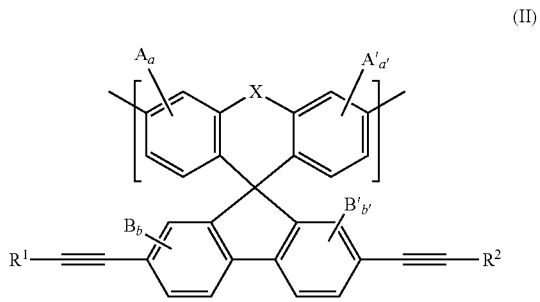
(II)

wherein A, A', B, B', a, a', b, b', R', $R^2$, and X are the same as in the formula (I).

3. The retardation film according to claim 1, wherein the optical film exhibits a birefringence index Δnxz of 0.005 to 0.070 with a wavelength of 550 nm, and
wherein Δnxz=nx−nz, nx denotes a refractive index in a direction for a maximum refractive index in a plane of the film (x-axis direction), and nz denotes a refractive index in the thickness direction of the film.

4. The retardation film according to claim 1, wherein the optical film exhibits Rth(450)/Rth(550)<1.06, and
wherein Rth(450) and Rth(550) denote a retardation value in the thickness direction with a wavelength of 450 nm and a wavelength of 550 nm, respectively.

5. The retardation film according to claim 1, wherein the optical film exhibits Rth(650)/Rth(550)>0.95, and
wherein Rth(550) and Rth(650) denote a retardation value in the thickness direction with a wavelength of 550 nm and a wavelength of 650 nm, respectively.

6. The retardation film according to claim 1, wherein the polymer is a polyester-based polymer.

7. The retardation film according to claim 1, wherein the optical film satisfies an index ellipsoid of nx≅ny>nz, and
wherein nx denotes a refractive index in a direction for a maximum refractive index in a plane of the film (x-axis direction), ny denotes a refractive index in a direction orthogonal to the x-axis direction in the plane (y-axis direction), and nz denotes a refractive index in the thickness direction of the film.

8. The retardation film according to claim 1, wherein the optical film satisfies an index ellipsoid of nx>ny>nz, and wherein nx denotes a refractive index in a direction for a maximum refractive index in a plane of the film (x-axis direction), ny denotes a refractive index in a direction orthogonal to the x-axis direction in the plane (y-axis direction), and nz denotes a refractive index in the thickness direction of the film.

9. The retardation film according to claim 1, wherein the optical film is composed of a coating film obtained by applying the polymer to a base material.

10. The retardation film according to claim 1, wherein a thickness of the optical film is 20 μm or less.

11. An image display device comprising the retardation film according to claim 1.

12. The retardation film according to claim 1, wherein the polymer further comprises a repeating unit represented by the following general formula (XIII) or (XIV):

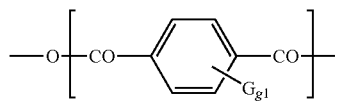

(XIII)

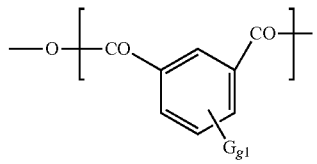

(XIV)

wherein G each independently denotes hydrogen, a halogen, an alkyl group having 1 to 4 carbon atoms, or a phenyl group, g1 denotes the number of substituents of the corresponding G and is an integer of 0 to 4.

13. The retardation film according to claim 12, wherein the polymer comprises both of the general formulae (XIII) and (XIV).

14. The retardation film according to claim 1, wherein $R^1$ and $R^2$ each independently denote a halogen or an $SiR^3R^4R^5$ group, wherein $R^3$ to $R^5$ each independently denote an alkyl group having 1 to 6 carbon atoms or an aryl group.

* * * * *